United States Patent [19]

Habenstein

[11] 4,184,850

[45] Jan. 22, 1980

[54] DIAGNOSTIC AGENT FOR THE DETECTION OF KETONE BODIES IN FLUIDS AND PROCESS FOR ITS MANUFACTURE

[75] Inventor: Klaus Habenstein, Wunstorf, Fed. Rep. of Germany

[73] Assignee: Behringwerke Aktiengesellschaft, Marburg, Fed. Rep. of Germany

[21] Appl. No.: 926,246

[22] Filed: Jul. 20, 1978

[30] Foreign Application Priority Data

Jul. 23, 1977 [DE] Fed. Rep. of Germany ....... 2733426

[51] Int. Cl.$^2$ .............................................. G01N 33/16
[52] U.S. Cl. .................................. 23/230 B; 252/408; 422/56
[58] Field of Search ....................... 23/230 B, 255 TP; 422/56; 252/408

[56] References Cited

U.S. PATENT DOCUMENTS

| | | | |
|---|---|---|---|
| 3,212,855 | 10/1965 | Mast | 23/253 TP |
| 4,097,240 | 6/1978 | Hirsch | 252/408 X |

OTHER PUBLICATIONS

Chemical Abstracts, 80: 67994x (1974).
Chemical Abstracts, 82: 121271r (1975).
Chemical Abstracts, 84: 27784e (1976).

*Primary Examiner*—Sidney Marantz
*Attorney, Agent, or Firm*—Curtis, Morris & Safford

[57] ABSTRACT

A diagnostic agent for the detection of ketones in fluids consisting of an absorbent carrier impregnated with sodium nitroferricyanide, a water-soluble lower amino acid, an alkaline buffer substance, and at least one organic acid, said organic acid serving to form a stabilizing environment around the sodium nitroferricyanide. The improved diagnostic agent may be produced by impregnating the carrier in a first step with an aqueous solution of the buffer substance and the amino acid, in a second step with a solution of an organic acid in an organic solvent and in a third step with a solution of sodium nitroferricyanide and a water-soluble organic acid in an organic solvent.

7 Claims, No Drawings

DIAGNOSTIC AGENT FOR THE DETECTION OF KETONE BODIES IN FLUIDS AND PROCESS FOR ITS MANUFACTURE

This invention relates to a diagnostic agent for the detection of ketone bodies in fluids, especially in body fluids, which agent consists of an absorbent carrier impregnated with sodium nitroferricyanide, a water-soluble amino acid and an alkaline buffer substance.

Ketone bodies are found in the urine of persons suffering from ketosis, i.e. a disorder of the carbohydrate-fat metabolism. An excess of acetyl-coenzyme A is condensed to acetoacetic acid from which acetone is formed in further reactions. The detection of these two ketone bodies in the urine is, therefore, of importance to the diagnosis and control of diabetes.

A very sensitive analytical process known for this purpose is the Legal test, but, because of the decomposition of sodium nitroferricyanide in alkaline solution, it can only be carried out with freshly prepared solutions and, hence, it is rather complicated. Later on, mixtures of the dry reagents have been compressed into tablets. But nowadays, detection is possible with test strips which are more easily to handle and which contain all reagents necessary for the reaction on an absorbent carrier (cf. U.S. Pat. No. 3,212,855 and GB-P No. 1,369,138).

The instability of sodium nitroferricyanide, which is only stable at a pH below 7 and which can be used for the test only in an alkaline medium at a pH above 8 is, however, still a problem of the test strips.

According to U.S. Pat. No. 3,212,855 the stability of the sodium nitroferricyanide is improved by the use of an organic, film-forming substance which protects the unstable compound from the basic buffer. A drawback of the test strips of this type is the reduced reaction speed.

As compared therewith, in British Pat. No. 1,369,138 a film-forming substance is not added and the paper impregnated with a basic buffer is first dried, then impregnated with a solution of sodium nitroferricy-anide in methanol and dimethyl formamide and dried again. Even after prolonged drying at 80° C., part of the dimethyl formamide having a relatively high boiling point remains on the carrier material where it probably exerts the stabilizing effect. The amount of dimethyl formamide retained on the test paper after drying strongly depends on the manufacturing conditions and, therefore, it is rather difficult to manufacture papers of constant reactivity. Moreover, dimethyl formamide is detrimental to health.

It is, therefore, the object of the present invention to provide a stable diagnostic agent for the detection of ketone bodies with uniform indication.

The diagnostic agent according to the invention, consisting of an absorbent carrier material impregnated with sodium nitroferricyanide, a water-soluble, low molecular weight amino acid and an alkaline buffer substance, is characterized by a content of at least one organic acid used to build up a stabilizing milieu for the sodium nitroferricyanide.

The stabilizing effect of the organic acids can be explained by the fact that with the access of a small amount of water, for example from the atmosphere, the alkaline buffer first reacts with the acids round the sodium nitroferricyanide so that the neutral to acid milieu around this compound is preserved. With the access of larger amounts of water, for example when a test is carried out, the alkaline buffer present in excess, after a rapidly proceeding ion reaction with the acids, establishes a weakly alkaline pH also in the region of the sodium nitroferricyanide, providing the most favorable conditions for the ketone detection. In this manner the advantage of the stabilizing effect of a micro-encapsulation is achieved without the reaction speed being reduced by the moisture withholding film of genuine micro-capsules.

The diagnostic agent according to the invention can be prepared by a process wherein the absorbent carrier is successively impregnated with the following solutions and dried after each impregnation step:
(a) an aqueous solution of the alkaline buffer substance and of a water-soluble low molecular weight amino acid;
(b) a solution in an organic solvent or solvent mixture of an organic acid soluble in an organic solvent;
(c) a solution in an organic solvent or solvent mixture of sodium nitroferricyanide, an organic acid soluble in water and in organic solvents and optionally an oxidation inhibitor, the alkaline buffer substance being applied to the absorbent carrier in an excess as regards equivalence over the sum of the organic acids contained in solutions (b) and (c).

Test papers prepared in this manner are very sensitive in their indication, flexible, they have good processing properties and a light basic color.

In principle, it is likewise possible to impregnate separately three thin absorbent carriers, each with one of the solutions (a), (b) and (c) and, after drying, to fix the impregnated papers, one on top of the other, with a holding device, for example by means of a fine net. It is preferred, however, to impregnate one carrier successively with the different solutions.

Preferred organic acids in solutions (b) and (c) are, for example, higher aliphatic monocarboxylic acids, aliphatic polycarboxylic acids, optionally substituted aromatic carboxylic acids and sulfonic acids, the acids being used either individually or in admixture with one another.

Examples of organic acids to be used according to the invention are: capric acid, caprylic acid, dodecylcarboxylic acid, oleic acid, oxalic acid, citric acid, malic acid, tartaric acid, salicylic acid, acetylsalicylic acid, 4-bromomethylbenzoic acid, 4-chlorobenzoic acid, 4-fluorobenzoic acid, 4-nitrobenzoic acid, 4-methoxyphenylacetic acid, diphenyldicarboxylic acid, phthalic acid, 4,5-dichlorophthalic acid, isophthalic acid, 5-nitroisophthalic acid, cinnamic acid and sulfosalicylic acid. The examples are not intended to limit the scope of the invention. An expert may obtain identical or similar results using equivalent compounds.

According to a preferred embodiment, an organic acid sparingly soluble in water and belonging to any one of the groups listed above is used for solution (b) and citric acid is used in solution (c).

The specified organic acids yield test papers that are especially stable to storage. It is stressed, however, that the process of the invention may also be carried out with other organic acids, for example those capable of forming polymers.

Suitable absorbent carrier materials are those known to the expert, for example papers or fleeces of animal, vegetable or man-made fibers.

Suitable lower, water-soluble amino acids are glycine and alanine.

As alkaline buffer substances, alkali metal and ammonium carbonates, phosphates and borates, alkali metal salts of ethylenediaminetetracetic acid and alkali metal salts of amino acids can be used. Good results are even obtained if a less than an equivalent amount of an alkali metal hydroxide is added to the lower water-soluble amino acid.

The choice of the organic solvent is not critical. There can be used, for example, lower alkanols, ethylglycol, toluene, tetramethylurea and dioxane, either individually or in admixture with one another.

By the addition of an oxidation inhibitor, for example 2-tert.butyl-4-methoxyphenol, a test agent is obtained having a very light basic color so that the sensitivity appears to be improved.

The following examples illustrate the invention but they are not intended to limit it thereto.

In the examples filter paper no. 2316 of Messrs. Schleicher and Schull was used which was dried at 80° C., after impregnation with solution (a), for 1 hour and, after impregnation with solutions (b) and (c), each time for 30 minutes.

EXAMPLE 1

For impregnation the following solutions are used:
Solution (a) 120 g of glycine, 28 g of sodium hydroxide and 300 ml of water
Solution (b) 6 g of oxalic acid, 150 ml of methanol and 150 ml of n-propanol
Solution (c) 3 g of sodium nitroferricyanide, 6 g of citric acid, 0.3 g of 2-tert.butyl-4-methoxyphenol, 150 ml of methanol and 150 ml of n-propanol.

The diagnostic paper obtained after final drying had a very light color and still indicated a content of 5 to 10 mg of acetoacetic acid in 100 ml of fluid and a content of 30 to 50 mg of acetone in 100 ml of fluid.

Papers of equally good quality were obtained by using in solution (b) oleic acid, 4,5-dichlorophthalic acid or sulfosalicyclic acid instead of oxalic acid.

EXAMPLE 2

For impregnation the following solutions were used:
Solution (a) as in Example 1
Solution (b) 6 g of oleic acid in 300 ml of toluene
Solution (c) as in Example 1.

The very light colored diagnostic paper obtained after final drying detected a content of 5 to 10 mg of acetoacetic acid in 100 ml of fluid.

Papers of equally good quality were obtained by using in solution (b) tetramethylurea, dioxane, ethylene glycol or propanol instead of toluene.

EXAMPLE 3

For impregnation the following solutions were used:
Solution (a) as in Example 1
Solution (b) 6 g of oleic acid and 300 ml of propanol
Solution (c) 3 g of sodium nitroferricyanide, 6 g of citric acid, 0.3 g of 2-tert.butyl-4-methoxyphenol, 150 ml of n-propanol and 150 ml of ethylglycol.

The diagnostic paper obtained detected a content of 5 to 10 mg of acetoacetic acid in 100 ml of fluid.

Papers of equally good quality were obtained by using in solution (c), instead of the solvent mixture, pure propanol or a mixture of methanol with the solvents specified in Example 2.

EXAMPLE 4

For impregnating the following solutions were used:
Solution (a) as in Example 1
Solution (b) 6 g of oleic acid and 300 ml of toluene
Solution (c) as in Example 1 but without the addition of 2-tert.-butyl-4-methoxyphenol.

The sensitivity of detection of the diagnostic paper obtained was slightly inferior to that of the paper of Example 2 but it still detected 10 to 15 ml of acetoacetic acid in 100 ml of fluid.

EXAMPLE 5

For impregnation the following solutions were used:
Solution (a) as in Example 1
Solution (b) 9 g of 4,5-dichlorophthalic acid, 150 ml of methanol and 150 ml of n-propanol
Solution (c) as in Example 1.

The diagnostic paper obtained was stored at 55° C. in closed boxes with a rolled rim. At the end of every second day the boxes were opened and the contents were subjected at room temperature to an atmosphere of 100% relative humidity for 10, 20 and 30 minutes, respectively. In each paper the content of sodium nitroferricyanide per square centimeter and the decrease thereof as a result of decomposition were determined. The results are indicated in the following Table 1. The content of 5 to 10 mg of acetoacetic acid per 100 ml of fluid was still detected by the stored papers by a weak but visible coloration. Even after a storage time of 29 days the papers only showed a slight yellow coloration.

Table 1

Decrease of the sodium nitroferricyanide content in a diagnostic paper impregnated by the process of the invention

| opening time of the boxes (min) | decrease in % after | | | |
|---|---|---|---|---|
| | 18 days | 22 days | 27 days | 29 days |
| 10 | 5 | 8.5 | 14.5 | 19 |
| 20 | | 8 | | 21.5 |
| 30 | 13.0 | 15.5 | 24.5 | 36 |

For comparison, a test paper impregnated according to German Pat. No. 2,158,125, Example 1 with
Solution (a)
25 g of glycine
36.3 g of sodium ethylenediaminetetraacetate
100 ml of water
Solution (b)
1.0 g of sodium nitroferricyanide
40 ml of dimethyl formamide
60 ml of methanol
was treated in the same manner and the results indicated in Table 2 were obtained. At the end of 12 days the very hard and slightly yellowish paper had acquired a brownish coloration and a content of 20 mg of acetoacetic acid in 100 ml of fluid was no longer detected therewith.

Table 2

Decrease of the sodium nitroferricyanide content (Process according to German Patent 2,158,125, Example 1)

| opening time of the boxes (min) | decrease in % after | |
|---|---|---|
| | 7 days | 12 days |
| 10 | 4.3 | 23.6 |
| 20 | 7.3 | 23.6 |
| 30 | 11.2 | 45.9 |

What is claimed is:

1. A diagnostic agent for the detection of ketone bodies in a fluid, said agent consisting of an absorbent carrier material impregnated with sodium nitroferricyanide, a water-soluble lower amino acid, an alkaline buffer substance, and at least one organic acid, said organic acid serving to form a stabilizing environment around the sodium nitroferricyanide.

2. The method of detecting ketone bodies in a fluid, which method comprises contacting said fluid with a diagnostic agent as in claim 1.

3. A method as in claim 2 wherein said fluid is a body fluid.

4. A method for making a diagnostic agent as claimed in claim 1, which comprises impregnating the absorbent carrier successively with the following solutions and drying the carrier after each impregnation step:
   (a) an aqueous solution of the alkaline buffer substance and of a water soluble low molecular weight amino acid;
   (b) a solution in an organic solvent or solvent mixture of an organic acid soluble in an organic solvent;
   (c) a solution in an organic solvent or solvent mixture of sodium nitroferricyanide and of an organic acid soluble in water and in organic solvents,
the alkaline buffer substance being applied to the absorbent carrier in an excess as regards equivalence over the sum of the organic acids contained in solutions (b) and (c).

5. The method as in claim 2 wherein solution (c) additionally contains an oxidation inhibitor.

6. The method as in claim 1, wherein solutions (b) and (c) contain at least one organic acid selected from the groups consisting of higher aliphatic monocarboxylic acids, aliphatic polycarboxylic acids, optionally substituted aromatic carboxylic acids and sulfonic acids.

7. The method as in claim 6, wherein solution (b) contains an organic acid that is sparingly soluble in water and solution (c) contains citric acid.

* * * * *